United States Patent [19]

Bouchette

[11] Patent Number: 4,615,937
[45] Date of Patent: Oct. 7, 1986

[54] ANTIMICROBIALLY ACTIVE, NON-WOVEN WEB USED IN A WET WIPER

[75] Inventor: Michael P. Bouchette, Appleton, Wis.

[73] Assignee: The James River Corporation, Richmond, Va.

[21] Appl. No.: 772,845

[22] Filed: Sep. 5, 1985

[51] Int. Cl.[4] .............................................. D04H 1/58
[52] U.S. Cl. ...................................... 428/288; 15/209; 424/25; 428/289; 428/290; 428/446; 428/452; 428/913; 604/360
[58] Field of Search ............... 428/446, 913, 288, 289, 428/290, 447, 451, 452; 604/359, 360; 15/209; 424/25; 206/812

[56] References Cited

U.S. PATENT DOCUMENTS

| | | | |
|---|---|---|---|
| 2,474,306 | 6/1949 | Doub | 260/212 |
| 2,702,780 | 2/1955 | Lerner | 167/84 |
| 3,138,533 | 6/1964 | Helm et al. | 167/84 |
| 3,227,614 | 1/1966 | Scheuer | 167/84 |
| 3,257,267 | 6/1966 | Hay | 162/159 |
| 3,264,172 | 8/1966 | Regotti | 162/161 |
| 3,567,118 | 3/1971 | Shepherd et al. | 424/28 |
| 3,624,224 | 11/1971 | Wei et al. | 424/28 |
| 3,728,213 | 4/1973 | Hinz | 424/28 |
| 3,860,709 | 1/1975 | Abbott et al. | 424/184 |
| 3,959,556 | 5/1976 | Morrison | 57/140 |
| 4,259,103 | 3/1981 | Malek et al. | 424/25 |
| 4,282,366 | 8/1981 | Eudy | 556/413 |
| 4,311,479 | 1/1982 | Fenn et al. | 8/495 |
| 4,343,853 | 8/1982 | Morrison | 428/233 |
| 4,394,378 | 7/1983 | Klein | 424/184 |
| 4,401,712 | 8/1983 | Morrison | 428/907 |
| 4,406,892 | 9/1983 | Eudy | 424/184 |
| 4,408,996 | 10/1983 | Baldwin | 424/184 |

FOREIGN PATENT DOCUMENTS 2103089 2/1983 United Kingdom .

OTHER PUBLICATIONS

Surface-Bonded Antimicrobial Activity of an Organosilicon Quaternary Ammonium Chloride, A. J. Isquith et al., Applied Microbiology, Dec. 1972, pp. 859-863.
Algicidal Activity of a Surface-Bonded Organosilicon Quaternary Ammonium Chloride, P. A. Walters, et al., Amer. Soc. for Microbiology, 1973.

Primary Examiner—James J. Bell
Attorney, Agent, or Firm—Finnegan, Henderson, Farabow, Garrett & Dunner

[57] ABSTRACT

An antimicrobially active, non-woven web, a wet wiper containing the web, and a method of making the web. The method includes the steps of forming an unbonded fibrous web; applying throughout the unbonded fibrous web an uncured binder and an antimicrobial agent, the antimicrobial active agent being substantive to the fibers of the web and to the binder; and curing the binder material to bind the fibers together to form an antimicrobially active, non-woven web. A preferred antimicrobial agent is an organo-silicon quaternary ammonium salt, especially a 3-(trimethoxylsilyl) propyldidecylmethyl ammonium chloride or a 3-(trimethoxysilyl) propyloctadecyldimethyl ammonium chloride.

12 Claims, No Drawings

ANTIMICROBIALLY ACTIVE, NON-WOVEN WEB USED IN A WET WIPER

BACKGROUND OF THE INVENTION

The present invention relates to non-woven webs and, more particularly, to antimicrobially active, non-woven webs, to wet wipers containing such a web, and to a method of making the web.

Wet wiper products, including those utilizing non-woven and air-laid webs, require antimicrobial properties to destroy or inhibit the growth of various microorganisms, bacteria, yeasts, and molds. Presently, there are at least four methods of treating the fabric of the wet wiper product to obtain some type of antimicrobial protection-sterilization; pore size control, such as Bacterial Filtration Efficiency (BFE); chemical surface treatment; and overall chemical protection. All of these methods have demonstrated inherent deficiencies for wet wiper products.

Sterilization may be achieved by sterilizing the raw materials going into the make-up of the product and/or sterilizing the final packaged product. Sterilization is an excellent technique for killing the microorganisms present to provide a microbiologically clean product for the intended use. However, in the case of wet wipers, sterilization as an antimicrobial technique is limited because once the product package has been opened to dispense the wipers, the sterilization is voided and any remaining wipers are exposed to and therefore subject to microbiological growth. As a result, the product is rendered both useless and potentially harmful.

Therefore, sterilization is viable only for single use packages of wet wipers. Nevertheless, due to shelf life and package integrity concerns, all single use wet wipers packages commercially available still rely on additional chemical protection for good microbiological control.

Fabric pore size control by BFE can be used to control the passage of microorganisms from one side or surface of the fabric through the fabric to the other side or surface. Pore size control as a method of microbiological transport control is generally used only with a dry fabric and is found most frequently in the medical industry in such products as CSR wraps and face masks. This method of microorganism transport control is ineffective for use in a wet wiper, because any microorganisms present can pass entirely around the fabric in the liquid or lotion phase of the product.

Antimicrobial surface treatment of a fabric may also be beneficial in the dry mode of usage, where, along with the pore size control by BFE, microorganisms are either filtered out and/or killed upon contact with the surface of the fabric. However, again in the case of wet wipers, surface treatment of the fabric has been shown to be insufficient to obtain the necessary microbiological control. The liquid or lotion phase of the wet wiper product penetrates into the interstices of the fabric to carry the microorganisms past the treated surface into the interstices of the fabric, where they may then grow and multiply.

Virtually the only method of antimicrobial control and protection presently used in wet wiper products is that which is achieved by a chemical permeation of preservative agents throughout the wet wiper product. This permeation may be achieved by padding the wiper fabric during its manufacture and/or by incorporating the chemicals in the liquid or lotion phase of the wiper product.

Padding the fabric is generally not used as a commercial technique because of the additional manufacturing processing costs. Since a liquid or lotion must be applied to the fabric anyway in a wet wiper product, and since the liquid or lotion without antimicrobial control or preservation agents represents a key opportunity for microbiological growth, the preferred method of applying the chemical preservation or antimicrobial control is to incorporate the soluble preservative agents in the lotion phase and then apply the preserved lotion to the fabric.

In either case, the end result is the same. Since the preservatives and antimicrobial agents are soluble in a liquid or lotion phase, they ultimately equilibrate throughout the wet wiper product and provide a homogenous chemical method of antimicrobial control. Unfortunately, when a wet wiper product of this type is ultimately used, the preservatives or antimicrobial agents remain behind on the user's skin from the liquid or lotion phase and leave an irritating residue on the skin. Many individuals exhibit adverse reactions to such preservatives, and hence, their enjoyable use of the wet wiper product is significantly impeded.

Moreover, both chemical solubility and antimicrobial spectrum activity considerations significantly limit the use of other, less harsh preservatives in the liquid wetting solution. Consequently, the present use of wet wiper products, such as those that use non-woven webs, has numerous inherent disadvantages.

Therefore, it would be desirable to incorporate the antimicrobial properties required in the wet wiper product in a manner substantive to and within the wet wiper fabric. In this manner, the issues of chemical solubility and antimicrobial activity considerations could be overcome because no harmful residue would be left on the skin of the user. In addition, the increased costs of padding the wet wiper fabric during its manufacturing process could be overcome by incorporating these substantive antimicrobials into the synthetic bonding agent typically already required for such non-woven fabrics.

In sum, present non-woven web products that exhibit antimicrobial activity are less than satisfactory. Often, the webs contain preservatives, that leave an irritating residue on the user's skin. Moreover, the use of various synthetic fibers and off-line treatment processes increase the cost of producing these non-woven web products.

SUMMARY OF THE INVENTION

Quite surprisingly, the inventor of the present invention has developed an antimicrobially active, non-woven web that overcomes the significant and inherent disadvantages present in previous non-woven webs that attempt to exhibit antimicrobial and wet wiper properties. Unlike previous webs, the non-woven web of the present invention need not be maintained in a preservative containing solution that contains irritating chemical and leaves harmful residues on the skin of the user. Moreover, the present invention utilizes currently existing and preferred processing techniques for application of the substantive antimicrobial agent, thereby reducing the cost of manufacture.

The present invention achieves these various advantages by providing a method for making an antimicrobially active, non-woven web. The method comprises the steps of: (a) forming an unbonded fibrous web; (b) applying throughout the unbonded fibrous web an uncured binder and an antimicrobial agent, the antimicrobial agent being substantive to the fibers of the web and to the binder when the web is either wet or dry; and (c) curing the binder to bind the fibers together to form an antimicrobially active, non-woven web. Preferably, the antimicrobial agent is an organo-silicon quaternary ammonium salt, such as a silylquaternary ammonium salt. Particularly preferred antimicrobial agents are 3-(trimethoxysilyl)propyldidecylmethyl ammonium salt and 3-(trimethoxysilyl)propyloctadecyldimethyl ammonium salt. Other such substantive antimicrobial agents may be recognized by those familiar with the art.

The antimicrobially active, non-woven web formed by the present invention comprises: (a) bonded fibers; (b) a binder substantially uniformly distributed on the fibers, the binder being present in an amount effective to bind the fibers; and (c) an antimicrobial agent substantially uniformly distributed on the fibers, the antimicrobial agent being substantive to the fibers and to the binder when the web is either wet or dry.

These non-woven webs can be used to form an antimicrobially active, wet wiper that comprises: (a) an antimicrobially active, non-woven web as defined above and (b) a substantially preservative free liquid in which the web is maintained in a wet condition until use.

The present invention overcomes the numerous inherent disadvantages commonly associated with previous antimicrobially active non-woven webs and obtains the various advantages of the invention. By no longer requiring the presence of a preservative in the surrounding solution, the non-woven web product of the present invention avoids leaving an irritating residue on the user's skin. Consequently, the present invention significantly advances over the state of the art.

The foregoing and other features and advantages of the present invention will be made more apparent from the following description of the preferred embodiments.

DESCRIPTION OF THE PREFERRED EMBODIMENTS

The method of the present invention produces an antimicrobially active, non-woven web. Initially, the present method forms an unbonded fibrous web. An uncured binder and an antimicrobial agent are then applied throughout the unbonded fibrous web, with the antimicrobial agent being substantive to both the fibers of the web and to the binder when the web is either wet or dry. After application of the binder and the antimicrobial agent, the binder is cured to bind the fibers together to form an antimicrobially active, non-woven web.

In accordance with the present invention, in the first step of the method, an unbonded fibrous web is formed. Although various cellulosic and synthetic fibers known in the art can be effectively used, the fibers are preferably cellulosic fibers and, more preferably, wood pulp fibers. The cellulosic fibers, such as wood pulp fibers, can be chemically treated and predried prior to forming, if desired. Examples of wood pulp fibers include various mechanical and chemical pulp fibers, such as cedar fibers, Southern pine fibers, spruce fibers, and hemlock fibers. The particular cellulosic fibers selected to make the non-woven web depend, in part, upon the type of texture, such as soft, woolly, or fluffy, and the porosity of the web that is desired. Alternatively, the fibers can be a combination of cellulosic and synthetic fibers.

The weight of the fibers, such as cellulosic fibers, used to form the unbonded fibrous web can vary depending upon the ultimate non-woven web that is produced. Typically, the weight of the fibers forming the web will vary within the range of about 5 lbs. per ream to about 60 lbs. per ream.

Various web forming techniques known in the art can be effectively used to form the unbonded fibers. The web can be formed by nonwoven techniques, such as air-laying the web or wet-laying the web. One type of apparatus for air forming fibers is shown in U.S. Pat. No. 4,292,271 to Buob et al. Other non-woven manufacturing techniques, such as melt blown, bonding, spun bonded, needle punched, and spun laced, may also be used along with the substantive antimicrobial agent to provide antimicrobially active webs. Some of the processing and cost benefits may be lost through the choice of these processes along with their concomitant raw materials limitations.

In accordance with the present invention, an uncured binder and an antimicrobial agent are applied throughout the unbonded fibrous web with the antimicrobial agent being substantive to the fibers of the web and to the binder when the web is either wet or dry. Various binders known in the art can be used. A preferred binder is a polymeric binder, such as a latex binder. Acceptable latex binders include acrylate emulsions, butadiene-styrene emulsions, ethylene vinyl acetate emulsions and acrylonitrile-butadiene emulsions. An especially effective latex binder is ethylene vinyl acetate, which is sold under the trademark AIRFLEX A-410 by Air Products, Inc. of Allentown, Pa. The binder can also include a mixture of anionic and nonionic binders, such as ethylene vinyl acetate, which is sold under the trademark AIRFLEX A-106 by Air Products, Inc. and ethylene acetate, sold under the trademark HA-8 by Rohm & Haas, of Philadelphia, Pa.

The amount of the binder that is to be applied to the fibers depends, in part, upon the type of fibers, such as cellulosic, and the antimicrobial agent being used in the non-woven web. Typically, the amount of the binder applied to the fibers varies within the range of about 5% to about 30%. Similarly, the amount of solids in the binder, especially a latex binder, depends, inter alia, on the weight of the fibers in the non-woven web. Generally, latex binders having from about 5% to about 25% solids are used. Of course, the skilled artisan can select the particular binder, the amount of the binder used, and the amount of solids present in the binder depending upon, in part, the type of fibers that are to be bound. The binder is applied to the fibers by various techniques known in the art, such as spraying, foaming, or padding.

The antimicrobial agent is selected to be substantive to both the fibers of the web and to the binder when the web is either wet or dry. As used herein, an antimicrobial agent is substantive if the antimicrobial agent attaches directly to the fibers of the web and to the binder without the need for an adhesive substance. Substantive antimicrobial agents do not substantially diffuse from the fibers or the binder used to bind the fibers together.

Preferred antimicrobial agents are organo-silicon quaternary ammonium salts, such as a silyl-quaternary ammonium salt. Preferred organo-silicon quaternary ammonium salts are 3-(trimethoxysilyl)propyldidecylmethyl ammonium salts, such as 3-(trimethoxysilyl)propyldidecylmethyl ammonium chloride, and 3-

(trimethoxysilyl)propyloctadecyldimethyl ammonium salts, such as 3-(trimethoxysilyl)propyloctadecyldimethyl ammonium chloride.

The antimicrobial agent is preferably applied to the fibrous web prior to or simultaneously with the application of the binder. Although various amounts of the antimicrobial agent are applied to the web depending upon, in part, the fibers selected and the particular binder used, the amount of the antimicrobial active agent is typically in the range of about 0.25% to about 3% of the total web weight.

The antimicrobial agent is selected to be substantive to the binder in addition to being substantive to the fibers of the web. Hence, such an antimicrobial agent attaches directly to the binder and the cellulosic fibers without the need for an adhesive substance. Likewise, the ionic character of the binder is carefully chosen so that the antimicrobial active agent is usually substantially inert with respect to the binder to prevent ionic interaction of the antimicrobial agent and the binder.

The antimicrobial agents can be prepared by various techniques known in the art. For example, U.S. Pat. Nos. 4,406,892 to Eudy, 4,282,366 to Eudy, 4,394,378 to Klein, and 4,408,996 to Baldwin describe various organo-silicon quaternary ammonium compounds, especially silyl quaternary ammonium compounds, and methods of preparing these compounds. Likewise, articles in the scientific literature, such as Walters et al., Algicidal Activity of a Surface-Bonded Organosilicon Quaternary Ammonium Chloride, 25 *Applied Microbiology*, 253-256 (1972) and Isquith et al., Surface-Bonded Antimicrobial Activity of an Organosilicon Quaternary Ammonium Chloride, 24 *Applied Microbiology*, 859-863 (1972), also disclose methods of making various organosilicon quaternary ammonium compounds. Thus, the skilled artisan can readily select a method of preparing the desired organosilicon quaternary ammonium compound.

The uncured binder and the antimicrobial agent are applied to the unbonded fibers in a manner that allows the binder and the antimicrobial agent to be present throughout the unbonded fibrous web and, hence, substantially uniformly distributed on the fibers. Accordingly, substantially all of the unbonded fibers of the web are to be contacted with the uncured binder and the antimicrobial agent during this application process.

Various application methods and apparatus, known in the art can be readily selected by the skilled artisan. For example, the uncured binder and the antimicrobial agent are sprayed onto unbound fibers, such as cellulosic fibers, that have been airlaid on a foraminous support. Similarly, the uncured binder and the antimicrobial agent can be contained in a bath through which the unbonded fibers pass. Other methods and apparatus include foaming and printing.

In accordance with the present invention, the binder material is cured to bind the fibers together to form an antimicrobial, non-woven web. Various curing techniques known in the art, such as infra-red radiation, electron beam, and forced hot air, can be effectively selected and used by the skilled artisan to achieve the proper degree of binder cure.

As a result, the present invention provides an antimicrobially active, non-woven web. The non-woven web has bonded fibers; a binder substantially uniformly distributed on the fibers, the binder being present in an amount effective to bind the fibers; and an antimicrobial agent substantially uniformly distributed on the fibers, the antimicrobial agent being substantive to the fibers and to the binder when the web is either wet or dry. The amount of the antimicrobial agent present within the non-woven web is preferably in the range of about 0.25% to about 3% of the total web weight. The amount of the binder present within the non-woven web is preferably in the range of about 5% to about 30% of the total web weight.

When the antimicrobially active, non-woven web of the present invention is present in a substantially preservative free liquid, an antimicrobial active wet wiper is achieved. The substantially preservative free liquid, such as water, maintains the web in a wet condition until use.

Other antimicrobial agents that are substantive to the fibers and the binder may also be used. In the case of wet wipers, the governing criteria are substantivity, antimicrobial activity, and safety, such that the wet wiper is safe for use on human skin and eyes.

The following is an example of the present invention, and it is intended to be merely exemplary.

EXAMPLE

An antimicrobially active, air-laid, non-woven web was prepared in accordance with the present invention. Unbonded cellulosic fibers were air-laid to produce an unbonded cellulosic fiber web of 40 pounds per ream. AIRFLEX 410, which is an acetate vinyl ethylene latex binder sold by Air Products, Inc. of Pennsylvania, and SIQUAT biocide were applied throughout the unbonded cellulosic fiber web as a combination of binder and antimicrobial agent. SIQUAT is 3-(trimethoxysilyl)propyldidecylmethyl ammonium chloride sold under the trademark SIQUAT by Sanitized Inc. Upon application, the antimicrobial agent was substantive both to the cellulosic fibers of the web and to the binder when the web is either wet or dry. The binder was then cured to bind the cellulosic fibers together.

The resulting air-laid, non-woven web was tested to determine its antimicrobial activity. Specifically, the non-woven web was tested to determine its effect on reduction and inhibition of five United States Pharmacopeia (U.S.P.) antimicrobial preservative effectiveness challenge organisms in a 28 day challenge test. The U.S.P. XX Preservative Effectiveness Test was modified to inoculate samples of the non-woven webs in the form of wet wiper towelettes. Those skilled in the art are readily familiar with the U.S.P. 28 day challenge test techniques and implications.

Basically, the wet wiper towelettes were subjected to an insult inoculation of five pathogenic microorganisms identified in the U.S.P. 28 day challenge test: *Aspergillus niger, Candida albicans, Staphylococcus aureus, Pseudomonas aeruginosa*, and *Escherichia coliformia* with total inoculation levels of $10^5$ to $10^6$ microorganisms/ml. The results of the 28 day challenge tests are provided in Table 1.

TABLE 1

|  | Inoculum level/gram | Average |
|---|---|---|
| Day 1 |  |  |
| An | $3.3 \times 10^4$/g | 267/g |
| Ca | $3.3 \times 10^4$/g | <33/g |
| Sa | $2.3 \times 10^6$/g | <33/g |
| Pa | $4.7 \times 10^5$/g | 33/g |
| Ec | $4.7 \times 10^5$/g | <33/g |
| WEEK 1 |  |  |
| An |  | 33/g |

TABLE 1-continued

| | Inoculum level/gram | Average |
|---|---|---|
| Ca | | <33/g |
| Sa | | <33/g |
| Pa | | <33/g |
| Ec | | <33/g |
| WEEK 2 | | |
| An | | <33/g |
| Ca | | <33/g |
| Sa | | <33/g |
| Pa | | <33/g |
| Ec | | <33/g |
| WEEK 3 | | |
| An | | <33/g |
| Ca | | <33/g |
| Sa | | <33/g |
| Pa | | <33/g |
| Ec | | <33/g |
| WEEK 4 Plated: | | |
| An | | <33/g |
| Ca | | <33/g |
| Sa | | 33/g |
| Pa | | 33/g |
| Ec | | 33/g |

The preservative is considered effective in the product examined if: (a) the concentration of viable bacteria is reduced to not more than 0.1% of the initial concentrations by the fourteenth day; (b) the concentrations of viable yeasts and molds remain at or below the initial concentrations during the first fourteen days; and (c) the concentration of each test microorganism remains at or below these designated levels during the remainder of the 28 day test period.

All five microorganisms reduced in numbers by a factor of $10^4$ or more. Accordingly, the antimicrobial activity of the towelettes was rated as being excellent.

Other embodiments of the invention will be apparent to one skilled in the art from a consideration of the specification or with the practice of the invention disclosed herein. It is intended that the specification and example be considered as exemplary only with the true scope and spirit of the invention being indicated by the claims.

What is claimed is:

1. An antimicrobially active, non-woven web comprising:
   (a) bonded fibers;
   (b) a binder substantially uniformly distributed on the fibers, the binder being present in an amount effective to bind the fibers; and
   (c) an antimicrobial agent substantially uniformly distributed on the fibers, the antimicrobial agent being substantive to the fibers and to the binder when the web is either wet or dry to prevent the antimicrobial agent from substantially diffusing from the fibers or the binder.

2. The web of claim 1, wherein the fibers are selected from the group consisting of cellulosic fibers, synthetic fibers, and combinations thereof.

3. The web of claim 1, wherein the binder is a polymeric binder.

4. The web of claim 3, wherein the polymeric binder is a latex binder.

5. The web of claim 1, wherein the antimicrobial agent is an organo-silicon quaternary ammonium salt.

6. The web of claim 5, wherein the organo-silicon quaternary ammonium salt is selected from the group consisting of a 3-(trimethoxysilyl)propyldidecylmethyl ammonium salt and 3-(trimethoxysilyl)propyloctadecyldimethyl ammonium salt.

7. The web of claim 6, wherein the salt has a chloride anion.

8. The web of claim 1, wherein the amount of the antimicrobial agent is in the range of 0.25% to about 3% of the total web weight.

9. The web of claim 1, wherein the amount of the binder is in the range of about 5% to about 30% of the total web weight.

10. The web of claim 1, wherein the antimicrobial agent is safe for contact with human skin and eyes.

11. The web of claim 1, wherein the bonded fibers are air-laid.

12. The web of claim 1, wherein the bonded fibers are wet-laid.

* * * * *

REEXAMINATION CERTIFICATE (1300th)

United States Patent [19]

Bouchette

[11] B1 4,615,937

[45] Certificate Issued  Jun. 5, 1990

[54] ANTIMICROBIALLY ACTIVE NON-WOVEN WEB USED IN A WET WIPER

[75] Inventor: Michael P. Bouchette, Appleton, Wis.

[73] Assignee: The James River Corp.

Reexamination Request:
No. 90/001,788, Jun. 13, 1989

Reexamination Certificate for:
Patent No.: 4,615,937
Issued: Oct. 7, 1986
Appl. No.: 772,845
Filed: Sep. 5, 1985

[51] Int. Cl.$^5$ .............................................. D04H 1/58
[52] U.S. Cl. .................. 428/288; 15/209 R; 424/443; 428/289; 428/290; 428/446; 428/452; 604/360
[58] Field of Search ............... 428/288, 289, 290, 446, 428/452, 913; 15/209 R; 604/360; 424/443

[56] References Cited
PUBLICATIONS

Steven F. Hayes, et al., "How Antimicrobial Treatment Can Improve Nonwovens", American Dyestuff Reporter, Jun. 1984, pp. 35–45.

*Primary Examiner*—James J. Bell

[57] ABSTRACT

An antimicrobially active, non-woven web, a wet wiper containing the web, and a method of making the web. The method includes the steps of forming an unbonded fibrous web; applying throughout the unbonded fibrous web an uncured binder and an antimicrobial agent, the antimicrobial active agent being substantive to the fibers of the web and to the binder; and curing the binder material to bind the fibers together to form an antimicrobially active, non-woven web. A preferred antimicrobial agent is an organo-silicon quaternary ammonium salt, especially a 3-(trimethoxylsilyl) propyldidecylmethyl ammonium chloride or a 3-(trimethoxysilyl)propyloctadecyldimethyl ammonium chloride.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-12 is confirmed.

* * * * *